US009795472B2

(12) United States Patent
Culbertson et al.

(10) Patent No.: US 9,795,472 B2
(45) Date of Patent: Oct. 24, 2017

(54) METHOD FOR CREATING INCISION TO IMPROVE INTRAOCULAR LENS PLACEMENT

(71) Applicant: OptiMedica Corporation, Santa Ana, CA (US)

(72) Inventors: William Culbertson, Miami, FL (US); Mark Blumenkranz, Portola Valley, CA (US); David Angeley, Charlottesville, VA (US); George Marcellino, Santa Cruz, CA (US); Michael Wiltberger, Santa Clara, CA (US); Dan Andersen, Menlo Park, CA (US)

(73) Assignee: Optimedica Corporation, Santa Ana, CA (US)

( * ) Notice: Subject to any disclaimer, the term of this patent is extended or adjusted under 35 U.S.C. 154(b) by 708 days.

(21) Appl. No.: 14/163,530

(22) Filed: Jan. 24, 2014

(65) Prior Publication Data
US 2014/0142558 A1    May 22, 2014

Related U.S. Application Data

(62) Division of application No. 12/703,689, filed on Feb. 10, 2010, now Pat. No. 8,657,810, which is a division
(Continued)

(51) Int. Cl.
*A61B 18/18*    (2006.01)
*A61F 2/16*    (2006.01)
*A61F 9/008*    (2006.01)

(52) U.S. Cl.
CPC .............. *A61F 2/1613* (2013.01); *A61F 2/16* (2013.01); *A61F 2/1637* (2013.01);
(Continued)

(58) Field of Classification Search
USPC ............................................................ 606/6
See application file for complete search history.

(56) References Cited

U.S. PATENT DOCUMENTS 4,169,664 A    10/1979  Bailey, Jr.
4,309,998 A    1/1982   Aron nee Rosa et al.
(Continued)

FOREIGN PATENT DOCUMENTS

EP    916320 A2    5/1999
EP    1279386 A1   1/2003
(Continued)

OTHER PUBLICATIONS

European Search Report for Application No. EP13164190, mailed on Jun. 18, 2013, 6 pages.
(Continued)

*Primary Examiner* — Nicole F Johnson
(74) *Attorney, Agent, or Firm* — Abbott Medical Optics Inc.

(57) ABSTRACT

A system and method for inserting an intraocular lens in a patient's eye includes a light source for generating a light beam, a scanner for deflecting the light beam to form an enclosed treatment pattern that includes a registration feature, and a delivery system for delivering the enclosed treatment pattern to target tissue in the patient's eye to form an enclosed incision therein having the registration feature. An intraocular lens is placed within the enclosed incision, wherein the intraocular lens has a registration feature that engages with the registration feature of the enclosed incision. Alternately, the scanner can make a separate registration incision for a post that is connected to the intraocular lens via a strut member.

21 Claims, 9 Drawing Sheets

Related U.S. Application Data of application No. 12/048,182, filed on Mar. 13, 2008, now Pat. No. 8,518,026.

(60) Provisional application No. 60/906,944, filed on Mar. 13, 2007.

(52) U.S. Cl.
CPC ........ *A61F 2/1648* (2013.01); *A61F 9/00825* (2013.01); *A61F 2002/1683* (2013.01); *A61F 2009/0087* (2013.01); *A61F 2009/0088* (2013.01); *A61F 2009/00859* (2013.01); *A61F 2009/00872* (2013.01); *A61F 2009/00887* (2013.01); *A61F 2009/00897* (2013.01)

(56) References Cited

U.S. PATENT DOCUMENTS

| | | |
|---|---|---|
| 4,538,608 A | 9/1985 | L'Esperance |
| 4,642,114 A | 2/1987 | Rosa |
| 4,917,486 A | 4/1990 | Raven et al. |
| 4,995,715 A | 2/1991 | Cohen |
| 5,098,426 A | 3/1992 | Sklar et al. |
| 5,112,328 A | 5/1992 | Taboada et al. |
| 5,171,320 A | 12/1992 | Nishi |
| 5,246,435 A | 9/1993 | Bille et al. |
| 5,257,988 A | 11/1993 | L'Esperance |
| 5,336,217 A | 8/1994 | Buys et al. |
| 5,391,165 A | 2/1995 | Fountain et al. |
| 5,437,658 A | 8/1995 | Muller et al. |
| 5,439,462 A | 8/1995 | Bille et al. |
| 5,459,570 A | 10/1995 | Swanson et al. |
| 5,460,396 A | 10/1995 | Sutter et al. |
| 5,493,109 A | 2/1996 | Wei et al. |
| 5,505,693 A | 4/1996 | Mackool |
| 5,520,679 A | 5/1996 | Lin |
| 5,702,441 A | 12/1997 | Zhou |
| 5,719,673 A | 2/1998 | Dorsel et al. |
| 5,720,894 A | 2/1998 | Neev et al. |
| 5,743,902 A | 4/1998 | Trost |
| 5,748,352 A | 5/1998 | Hattori |
| 5,748,898 A | 5/1998 | Ueda |
| 5,779,696 A | 7/1998 | Berry et al. |
| 5,795,295 A | 8/1998 | Hellmuth et al. |
| 5,865,830 A | 2/1999 | Parel et al. |
| 5,906,611 A | 5/1999 | Dodick et al. |
| 5,957,915 A | 9/1999 | Trost |
| 5,971,978 A | 10/1999 | Mukai |
| 5,980,513 A | 11/1999 | Frey et al. |
| 5,984,916 A | 11/1999 | Lai |
| 5,993,438 A | 11/1999 | Juhasz et al. |
| 6,002,127 A | 12/1999 | Vestal et al. |
| 6,004,314 A | 12/1999 | Wei et al. |
| 6,019,472 A | 2/2000 | Koester et al. |
| 6,053,613 A | 4/2000 | Wei et al. |
| 6,057,543 A | 5/2000 | Vestal et al. |
| 6,099,522 A | 8/2000 | Knopp et al. |
| 6,110,166 A | 8/2000 | Juhasz |
| 6,111,645 A | 8/2000 | Tearney et al. |
| 6,146,375 A | 11/2000 | Juhasz et al. |
| 6,149,644 A | 11/2000 | Xie |
| 6,197,059 B1 | 3/2001 | Cumming |
| 6,210,401 B1 | 4/2001 | Lai |
| 6,254,595 B1 | 7/2001 | Juhasz et al. |
| 6,281,493 B1 | 8/2001 | Vestal et al. |
| 6,322,556 B1 | 11/2001 | Gwon et al. |
| 6,324,191 B1 | 11/2001 | Horvath |
| 6,325,792 B1 | 12/2001 | Swinger et al. |
| 6,328,733 B1 | 12/2001 | Trost |
| RE37,504 E | 1/2002 | Lin |
| 6,344,040 B1 | 2/2002 | Juhasz et al. |
| RE37,585 E | 3/2002 | Mourou et al. |
| 6,373,571 B1 | 4/2002 | Juhasz et al. |
| 6,396,587 B1 | 5/2002 | Knupfer et al. |
| D459,806 S | 7/2002 | Webb |
| D459,807 S | 7/2002 | Webb |
| D462,442 S | 9/2002 | Webb |
| D462,443 S | 9/2002 | Webb |
| 6,454,761 B1 | 9/2002 | Freedman |
| 6,497,701 B2 | 12/2002 | Shimmick et al. |
| 6,610,050 B2 | 8/2003 | Bille |
| 6,623,476 B2 | 9/2003 | Juhasz et al. |
| 6,638,271 B2 | 10/2003 | Munnerlyn et al. |
| 6,648,877 B1 | 11/2003 | Juhasz et al. |
| 6,652,511 B1 | 11/2003 | Tomita |
| 6,676,653 B2 | 1/2004 | Juhasz et al. |
| 6,693,927 B1 | 2/2004 | Horvath et al. |
| 6,706,036 B2 | 3/2004 | Lai |
| 6,751,033 B2 | 6/2004 | Goldstein et al. |
| 6,754,419 B2 | 6/2004 | Ide et al. |
| 6,902,561 B2 | 6/2005 | Kurtz et al. |
| 6,984,227 B2 | 1/2006 | Munnerlyn et al. |
| 7,027,233 B2 | 4/2006 | Goldstein et al. |
| 7,146,983 B1 | 12/2006 | Hohla et al. |
| 7,220,255 B2 | 5/2007 | Lai |
| 7,562,148 B2 | 7/2009 | Metke et al. |
| 7,662,148 B2 | 2/2010 | Kuhn et al. |
| 7,717,907 B2 | 5/2010 | Ruiz et al. |
| 7,766,903 B2 | 8/2010 | Blumenkranz et al. |
| 8,186,357 B2 | 5/2012 | Lubatschowski et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 9,233,023 B2 | 1/2016 | Culbertson et al. |
| 9,233,024 B2 | 1/2016 | Culbertson et al. |
| 2001/0010003 A1 | 7/2001 | Lai |
| 2001/0016771 A1 | 8/2001 | Cumming |
| 2002/0103478 A1 | 8/2002 | Gwon et al. |
| 2002/0128637 A1 | 9/2002 | von der Heide et al. |
| 2003/0053219 A1 | 3/2003 | Manzi |
| 2003/0060880 A1 | 3/2003 | Feingold |
| 2003/0098834 A1 | 5/2003 | Ide et al. |
| 2003/0125718 A1 | 7/2003 | Munnerlyn et al. |
| 2004/0148022 A1 | 7/2004 | Eggleston |
| 2004/0199149 A1 | 10/2004 | Myers et al. |
| 2004/0199150 A1 | 10/2004 | Lai |
| 2004/0243112 A1 | 12/2004 | Bendett et al. |
| 2005/0015143 A1 | 1/2005 | Willis et al. |
| 2005/0165387 A1 | 7/2005 | Lubatschowski et al. |
| 2005/0187623 A1 | 8/2005 | Tassignon |
| 2006/0041308 A1 | 2/2006 | Nichamin |
| 2006/0047339 A1 | 3/2006 | Brown |
| 2006/0100677 A1 | 5/2006 | Blumenkranz et al. |
| 2006/0106372 A1 | 5/2006 | Kuhn et al. |
| 2006/0195076 A1 | 8/2006 | Blumenkranz et al. |
| 2006/0235428 A1 | 10/2006 | Silvestrini |
| 2007/0173794 A1 | 7/2007 | Frey et al. |
| 2007/0173795 A1 | 7/2007 | Frey et al. |
| 2007/0185475 A1 | 8/2007 | Frey et al. |
| 2008/0058841 A1 | 3/2008 | Kurtz et al. |
| 2008/0281303 A1 | 11/2008 | Culbertson et al. |
| 2008/0281413 A1* | 11/2008 | Culbertson ............ A61F 9/008 623/6.12 |
| 2009/0012507 A1 | 1/2009 | Culbertson et al. |
| 2010/0137850 A1 | 6/2010 | Culbertson et al. |
| 2010/0137982 A1 | 6/2010 | Culbertson et al. |
| 2010/0137983 A1 | 6/2010 | Culbertson et al. |
| 2010/0191226 A1 | 7/2010 | Blumenkranz et al. |
| 2011/0184392 A1 | 7/2011 | Culbertson et al. |
| 2011/0319873 A1 | 12/2011 | Raksi et al. |
| 2011/0319875 A1 | 12/2011 | Loesel et al. |

FOREIGN PATENT DOCUMENTS

| | | |
|---|---|---|
| EP | 1364632 A1 | 11/2003 |
| EP | 0983757 B1 | 7/2006 |
| JP | H0197450 A | 4/1989 |
| JP | H0323857 A | 1/1991 |
| JP | H1097450 A | 4/1998 |
| JP | 2006288770 A | 10/2006 |
| WO | WO-9308877 A1 | 5/1993 |
| WO | 9407435 A1 | 4/1994 |
| WO | WO-9407424 A1 | 4/1994 |

(56) References Cited

FOREIGN PATENT DOCUMENTS

| WO | WO-2006074469 A2 | 7/2000 |
|----|------------------|--------|
| WO | WO-0164135 A1 | 9/2001 |
| WO | WO-2006074469 A3 | 10/2007 |
| WO | WO-2008030718 A2 | 3/2008 |

OTHER PUBLICATIONS

European Search Report for Application No. EP13164193, mailed on Jun. 25, 2013, 6 pages.
European Search Report for Application No. EP13164195, mailed on Jun. 28, 2013, 6 pages.
Extended European Search Report for Application No. EP14177176.6, mailed on Dec. 15, 2014, 7 pages.
Abstract of AU Publication No. 2007292491. Publication Date Mar. 13, 2008. which is the AU counterpart of the WO08030718 A2 application.
Baikoff G., et al., "Contact Between 3 Phakic Intraocular Lens Models and the Crystalline Lens: An Anterior Chamber Optical Coherence Tomography Study," Journal of Cataract and Refractive Surgery, 2004, vol. 430 (9), pp. 2007-2012.
Co-pending U.S. Appl. No. 12/048,182, filed Mar. 13, 2008.
Co-pending U.S. Appl. No. 12/048,185, filed Mar. 13, 2008.
Co-pending U.S. Appl. No. 12/048,186, filed Mar. 13, 2008.
Co-pending U.S. Appl. No. 12/510,148, filed Jul. 27, 2009.
Co-pending U.S. Appl. No. 12/703,687, filed Feb. 10, 2010.
Co-pending U.S. Appl. No. 12/703,689, filed Feb. 10, 2010.
Co-pending U.S. Appl. No. 13/569,103, filed Aug. 7, 2012.
Geerling G., et al., "Initial Clinical Experience with the Picosecond Nd:YLF Laser for Intraocular Therapeutic Applications," British Journal of Opthalmology, 1998, vol. 82, vol. 8 (5), pp. 504-509.
Gimbel H.V., et al., "Continuous Curvilinear Capsulorhexis," Journal of Cataract and Refractive Sugery, 1991, vol. 17 (1), pp. 110-111.
Gimbel H.V., et al., "Development Advantages and Methods of the Continuous Circular Capsulorhexis Technique," Journal of Cataract and Refractive Surgery, 1990, vol. 16 (1), pp. 31-37.
Gimbel H.V., et al., "Principles of Nuclear Phaco Emulsification"In; Cataract Surgery Techniques Complications and Management, 2nd Edition., Steinert et al., 2004, Chap. 15, pp. 153-181.
International Search Report and Written Opinion for Application No. PCT/US08/03382, mailed on Jul. 25, 2008, 5 pages.
International Search Report and Written Opinion for Application No. PCT/US08/03385, mailed on Jul. 25, 2008, 5 pages.
Izatt J.A., et al., "Micrometer-Scale Resolution Imaging of the Anterior Eye In Vivo With Optical Coherence Tomography," Arch Ophthalmology, 1994, vol. 112 (12), pp. 1584-1589.
Office Action mailed Aug. 4, 2011 for European Application No. 08726825.6 filed Mar. 13, 2008.
Office Action mailed Aug. 6, 2012 for European Application No. 08726825.6 filed Mar. 13, 2008.
Office Action mailed Jun. 15, 2011 for European Application No. 08726822.3 filed Mar. 13, 2008.
Steinert et al., "Neodymium: Yttrium-Aluminum-Garnet Laser Posterior Capsulotomy"In: Cataract Surgery Techniques Complications and Management, 2nd Edition., Steinert et al., 2004, Chap, 44, pp. 531-544.
Supplementary European Search Report for Application No. EP08726822, mailed on Apr. 9, 2010, 6 pages.
Supplementary European Search Report for Application No. EP08726825, mailed on Apr. 30, 2010, 8 pages.

* cited by examiner

METHOD FOR CREATING INCISION TO IMPROVE INTRAOCULAR LENS PLACEMENT

RELATED APPLICATIONS

This application is divisional of U.S. application Ser. No. 12/783,689, abandoned, which is a divisional of U.S. application Ser. No. 12/048,182, filed Mar. 13, 2008, which issued as U.S. Pat. No. 8,518,026, which claims the benefit of priority of U.S. Provisional Application No. 60/906,944, filed Mar. 13, 2007, all of which are incorporated herein by reference in their entirety.

FIELD OF THE INVENTION

The present invention relates to ophthalmic surgical procedures and systems.

BACKGROUND OF THE INVENTION

Cataract extraction is one of the most commonly performed surgical procedures in the world with estimated 2.5 million cases performed annually in the United States and 9.1 million cases worldwide in 2000. This was expected to increase to approximately 13.3 million estimated global cases in 2006. This market is composed of various segments including intraocular lenses for implantation, viscoelastic polymers to facilitate surgical maneuvers, disposable instrumentation including ultrasonic phacoemulsification tips, tubing, and various knives and forceps. Modern cataract surgery is typically performed using a technique termed phacoemulsification in which an ultrasonic tip with an associated water stream for cooling purposes is used to sculpt the relatively hard nucleus of the lens after performance of an opening in the anterior lens capsule termed anterior capsulotomy or more recently capsulorhexis. Following these steps as well as removal of residual softer lens cortex by aspiration methods without fragmentation, a synthetic foldable intraocular lens (IOL) is inserted into the eye through a small incision.

One of the earliest and most critical steps in the procedure is the performance of capsulorhexis. This step evolved from an earlier technique termed can-opener capsulotomy in which a sharp needle was used to perforate the anterior lens capsule in a circular fashion followed by the removal of a circular fragment of lens capsule typically in the range of 5-8 mm in diameter. This facilitated the next step of nuclear sculpting by phacoemulsification. Due to a variety of complications associated with the initial can-opener technique, attempts were made by leading experts in the field to develop a better technique for removal of the anterior lens capsule preceding the emulsification step. The concept of the capsulorhexis is to provide a smooth continuous circular opening through which not only the phacoemulsification of the nucleus can be performed safely and easily, but also for easy insertion of the intraocular lens. It provides both a clear central access for insertion, a permanent aperture for transmission of the image to the retina by the patient, and also a support of the IOL inside the remaining capsule that would limit the potential for dislocation.

Using the older technique of can-opener capsulotomy, or even with the continuous capsulorhexis, problems may develop related to inability of the surgeon to adequately visualize the capsule due to lack of red reflex, to grasp it with sufficient security, to tear a smooth circular opening of the appropriate size without radial rips and extensions or technical difficulties related to maintenance of the anterior chamber depth after initial opening, small size of the pupil, or the absence of a red reflex due to the lens opacity. Some of the problems with visualization have been minimized through the use of dyes such as methylene blue or indocyanine green. Additional complications arise in patients with weak zonules (typically older patients) and very young children that have very soft and elastic capsules, which are very difficult to mechanically rupture.

Many cataract patients are astigmatic. Astigmatism can occur when the cornea has a different curvature one direction than the other. IOLS are used for correcting astigmatism but require precise placement, orientation, and stability. Complete and long lasting correction using IOLs is difficult. Further, IOLs are not presently used to correct beyond 5D of astigmatism, even though many candidates have more severe aberrations. Correcting it further often involves making the corneal shape more spherical, or at least more radially symmetrical. There have been numerous approaches, including Corneaplasty, Astigmatic Keratotomy (AK), Corneal Relaxing Incisions (CRI), and Limbal Relaxing Incisions (LRI). All are done using manual, mechanical incisions. Presently, astigmatism cannot easily or predictably be fully corrected. About one third of those who have surgery to correct the irregularity find that their eyes regress to a considerable degree and only a small improvement is noted. Another third find that the astigmatism has been significantly reduced but not fully corrected. The remaining third have the most encouraging results with the most or all of the desired correction achieved.

What is needed are ophthalmic methods, techniques and apparatus to advance the standard of care of the astigmatic cataract patient.

SUMMARY OF THE INVENTION

The present invention provides methods and apparatus to precisely and accurately seat an IOL within the capsule of an eye of a patient by using a short pulse laser to create a capsular incision whose size and shape complement that of the IOL itself. This can be accomplished by adding asymmetrical features to the incision and lens, or portions thereof.

A method of inserting an intraocular lens in a patient's eye includes generating a light beam, deflecting the light beam using a scanner to form an enclosed treatment pattern that includes a registration feature, delivering the enclosed treatment pattern to target tissue in the patient's eye to form an enclosed incision therein having the registration feature, and placing an intraocular lens within the enclosed incision, wherein the intraocular lens has a registration feature that engages with the registration feature of the enclosed incision.

A method of inserting an intraocular lens in a patient's eye includes generating a light beam, deflecting the light beam using a scanner to form an enclosed treatment pattern and a registration pattern, delivering the enclosed treatment pattern and the second pattern to target tissue in the patient's eye to form an enclosed incision and a registration incision therein, placing an intraocular lens within the enclosed incision, placing a post within the registration incision, and connecting the post to the intraocular lens using at least one strut member.

Other objects and features of the present invention will become apparent by a review of the specification, claims and appended figures.

DETAILED DESCRIPTION OF THE PREFERRED EMBODIMENTS

The techniques and systems disclosed herein provide many advantages over the current standard of care. Specifically, rapid and precise openings in the lens capsule are enabled using 3-dimensional patterned laser cutting to facilitate the placement and stability of intraocular lenses.

Another procedure enabled by the techniques described herein provides for the controlled formation of an incision in the anterior and/or posterior lens capsule. Conventional procedures require a complete circle or nearly complete circular cut. Openings formed using conventional, manual capsulorhexis techniques rely primarily on the mechanical shearing properties of lens capsule tissue and uncontrollable tears of the lens capsule to form openings. These conventional techniques are confined to the central lens portion or to areas accessible using mechanical cutting instruments and to varying limited degrees utilize precise anatomical measurements during the formation of the tears. In contrast, the controllable, patterned laser techniques described herein may be used to create an incision in virtually any position in the anterior and/or posterior capsule(s) and in virtually any shape. In "Bag-in-the-lens" surgery, matching incisions must be made in both the anterior and posterior capsules to fit the IOL in place. The present invention is uniquely suited to perform such matching incisions.

Furthermore, these capsular incisions may be tailored or keyed to accommodate an asymmetric IOL that requires it to be precisely positioned in both its location and rotational orientation. Moreover, the controllable, patterned laser techniques described herein also have available and/or utilize precise lens capsule size, measurement and other dimensional information that allows the incision or opening formation while minimizing impact on surrounding tissue.

Figure 1:
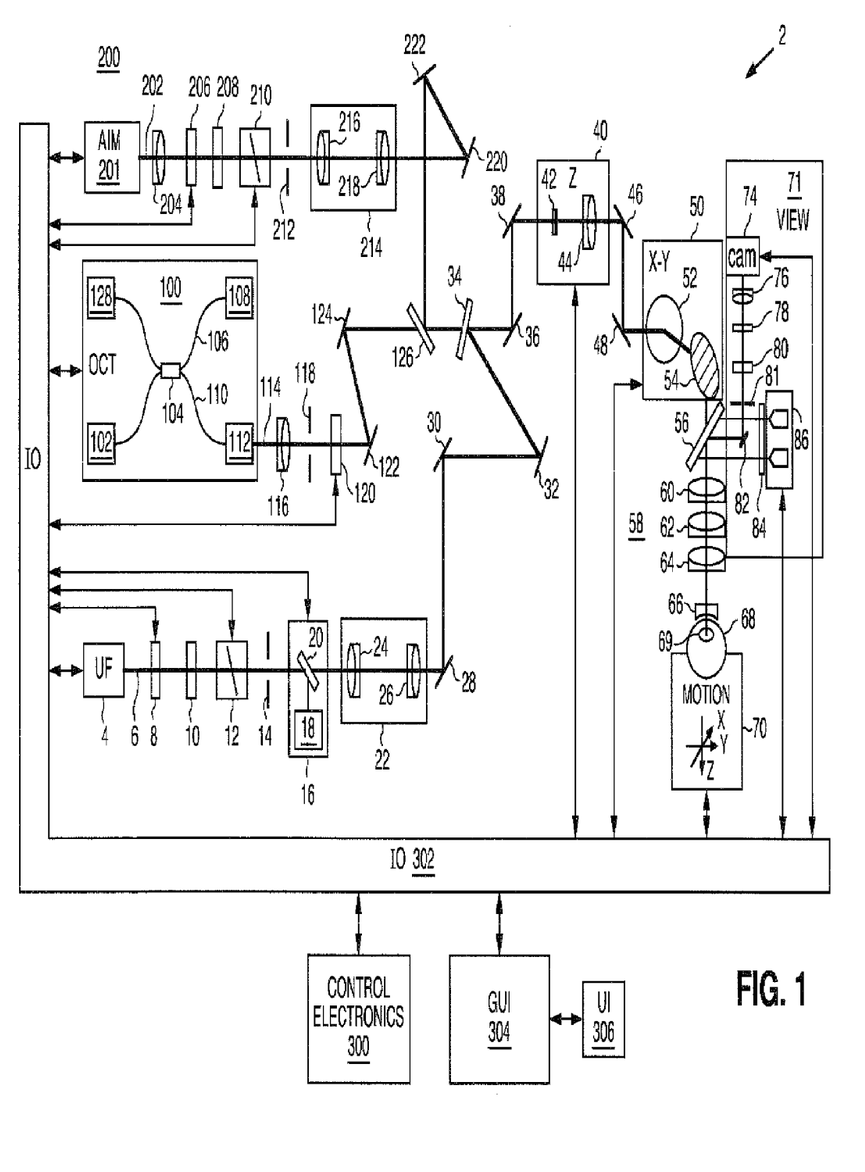
FIG. 1 is a schematic diagram of the optical beam scanning system.

The present invention can be implemented by a system that projects or scans an optical beam into a patient's eye 68, such as system 2 shown in FIG. 1 which includes an ultrafast (UF) light source 4 (e.g. a femtosecond laser). Using this system, a beam may be scanned in a patient's eye in three dimensions: X, Y, Z. In this embodiment, the UF wavelength can vary between 1010 nm to 1100 nm and the pulse width can vary from 100 fs to 10000 fs. The pulse repetition frequency can also vary from 10 kHz to 250 kHz. Safety limits with regard to unintended damage to non-targeted tissue bound the upper limit with regard to repetition rate and pulse energy; while threshold energy, time to complete the procedure and stability bound the lower limit for pulse energy and repetition rate. The peak power of the focused spot in the eye 68 and specifically within the crystalline lens 69 and anterior capsule of the eye is sufficient to produce optical breakdown and initiate a plasma-mediated ablation process. Near-infrared wavelengths are preferred because linear optical absorption and scattering in biological tissue is reduced across that spectral range. As an example, laser 4 may be a repetitively pulsed 1035 nm device that produces 500 fs pulses at a repetition rate of 100 kHz and an individual pulse energy in the ten microjoule range.

The laser 4 is controlled by control electronics 300, via an input and output device 302, to create optical beam 6. Control electronics 300 may be a computer, microcontroller, etc. In this example, the entire system is controlled by the controller 300, and data moved through input/output device IO 302. A graphical user interface GUI 304 may be used to set system operating parameters, process user input (UI) 306 on the GUI 304, and display gathered information such as images of ocular structures.

The generated UF light beam 6 proceeds towards the patient eye 68 passing through half-wave plate, 8, and linear polarizer, 10. The polarization state of the beam can be adjusted so that the desired amount of light passes through half-wave plate 8 and linear polarizer 10, which together act as a variable attenuator for the UF beam 6. Additionally, the orientation of linear polarizer 10 determines the incident polarization state incident upon beamcombiner 34, thereby optimizing beamcombiner throughput.

The UF beam proceeds through a shutter 12, aperture 14, and a pickoff device 16. The system controlled shutter 12 ensures on/off control of the laser for procedural and safety reasons. The aperture sets an outer useful diameter for the laser beam and the pickoff monitors the output of the useful beam. The pickoff device 16 includes of a partially reflecting mirror 20 and a detector 18. Pulse energy, average power, or a combination may be measured using detector 18. The information can be used for feedback to the half-wave plate 8 for attenuation and to verify whether the shutter 12 is open or closed. In addition, the shutter 12 may have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a 2 element beam expanding telescope comprised of spherical optics 24 and 26 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the optical system 22 can be used to image aperture 14 to a desired location (e.g. the center location between the 2-axis scanning device 50 described below). In this way, the amount of light that makes it through the aperture 14 is assured to make it through the scanning system. Pickoff device 16 is then a reliable measure of the usable light.

After exiting conditioning stage 22, beam 6 reflects off of fold mirrors 28, 30, & 32. These mirrors can be adjustable for alignment purposes. The beam 6 is then incident upon beam combiner 34. Beamcombiner 34 reflects the UF beam 6 (and transmits both the OCT 114 and aim 202 beams described below). For efficient beamcombiner operation, the angle of incidence is preferably kept below 45 degrees and the polarization where possible of the beams is fixed. For the UF beam 6, the orientation of linear polarizer 10 provides fixed polarization.

Following the beam combiner 34, the beam 6 continues onto the z-adjust or Z scan device 40. In this illustrative example the z-adjust includes a Galilean telescope with two lens groups 42 and 44 (each lens group includes one or more lenses). Lens group 42 moves along the z-axis about the collimation position of the telescope. In this way, the focus position of the spot in the patient's eye 68 moves along the z-axis as indicated. In general there is a fixed linear relationship between the motion of lens 42 and the motion of the focus. In this case, the z-adjust telescope has an approximate 2× beam expansion ratio and a 1:1 relationship of the movement of lens 42 to the movement of the focus. Alternatively, lens group 44 could be moved along the z-axis to actuate the z-adjust, and scan. The z-adjust is the z-scan device for treatment in the eye 68. It can be controlled automatically and dynamically by the system and selected to be independent or to interplay with the X-Y scan device described next. Mirrors 36 and 38 can be used for aligning the optical axis with the axis of z-adjust device 40.

After passing through the z-adjust device 40, the beam 6 is directed to the x-y scan device by mirrors 46 & 48. Mirrors 46 & 48 can be adjustable for alignment purposes. X-Y scanning is achieved by the scanning device 50 preferably using two mirrors 52 & 54 under the control of control electronics 300, which rotate in orthogonal directions using motors, galvanometers, or any other well known optic moving device. Mirrors 52 & 54 are located near the telecentric position of the objective lens 58 and contact lens 66 combination described below. Tilting these mirrors 52/54 causes them to deflect beam 6, causing lateral displacements in the plane of UF focus located in the patient's eye 68. Objective lens 58 may be a complex multi-element lens element, as shown, and represented by lenses 60, 62, and 64. The complexity of the lens 58 will be dictated by the scan field size, the focused spot size, the available working distance on both the proximal and distal sides of objective 58, as well as the amount of aberration control. An f-theta lens 58 of focal length 60 mm generating a spot size of 10 µm, over a field of 10 mm, with an input beam size of 15 mm diameter is an example. Alternatively, X-Y scanning by scanner 50 may be achieved by using one or more moveable optical elements (e.g. lenses, gratings) which also may be controlled by control electronics 300, via input and output device 302.

The aiming and treatment scan patterns can be automatically generated by the scanner 50 under the control of controller 300. Such patterns may be comprised of a single spot of light, multiple spots of light, a continuous pattern of light, multiple continuous patterns of light, and/or any combination of these. In addition, the aiming pattern (using aim beam 202 described below) need not be identical to the treatment pattern (using light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional contact lens 66, which can be any suitable ophthalmic lens, can be used to help further focus the optical beam 6 into the patient's eye 68 while helping to stabilize eye position. The positioning and character of optical beam 6 and/or the scan pattern the beam 6 forms on the eye 68 may be further controlled by use of an input device such as a joystick, or any other appropriate user input device (e.g. GUI 304) to position the patient and/or the optical system.

The UF laser 4 and controller 300 can be set to target the surfaces of the targeted structures in the eye 68 and ensure that the beam 6 will be focused where appropriate and not unintentionally damage non-targeted tissue. Imaging modalities and techniques described herein, such as for example, Optical Coherence Tomography (OCT), Purkinje imaging, Scheimpflug imaging, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, Optical Coherence Tomography (OCT), Purkinje imaging, Scheimpflug imaging, ultrasound, or other known ophthalmic or medical imaging modalities and/or combinations thereof. In the embodiment of FIG. 1, an OCT device 100 is described, although other modalities are within the scope of the present invention. An OCT scan of the eye will provide information about the axial location of the anterior and posterior lens capsule, the boundaries of the cataract nucleus, as well as the depth of the anterior chamber. This information is then be loaded into the control electronics 300, and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device 100 in FIG. 1 includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the UF laser system. The return signals from both the reference and sample arms 106, 110 are then directed by coupler 104 to a detection device 128, which employs either time domain, frequency or single point detection techniques. In FIG. 1, a frequency domain technique is used with an OCT wavelength of 920 nm and bandwidth of 100 nm.

Exiting connector 112, the OCT beam 114 is collimated using lens 116. The size of the collimated beam 114 is determined by the focal length of lens 116. The size of the beam 114 is dictated by the desired NA at the focus in the eye and the magnification of the beam train leading to the eye 68. Generally, OCT beam 114 does not require as high an NA as the UF beam 6 in the focal plane and therefore the OCT beam 114 is smaller in diameter than the UF beam 6 at the beamcombiner 34 location. Following collimating lens 116 is aperture 118 which further modifies the resultant NA of the OCT beam 114 at the eye. The diameter of aperture 118 is chosen to optimize OCT light incident on the target tissue and the strength of the return signal. Polarization control element 120, which may be active or dynamic, is used to compensate for polarization state changes which may be induced by individual differences in corneal birefringence, for example. Mirrors 122 & 124 are then used to direct the OCT beam 114 towards beamcombiners 126 & 34. Mirrors 122 & 124 may be adjustable for alignment purposes and in particular for overlaying of OCT beam 114 to UF beam 6 subsequent to beamcombiner 34. Similarly, beamcombiner 126 is used to combine the OCT beam 114 with the aim beam 202 described below.

Once combined with the UF beam 6 subsequent to beamcombiner 34, OCT beam 114 follows the same path as UF beam 6 through the rest of the system. In this way, OCT beam 114 is indicative of the location of UF beam 6. OCT beam 114 passes through the z-scan 40 and x-y scan 50 devices then the objective lens 58, contact lens 66 and on into the eye 68. Reflections and scatter off of structures within the eye provide return beams that retrace back through the optical system, into connector 112, through coupler 104, and to OCT detector 128. These return back reflections provide the OCT signals that are in turn interpreted by the system as to the location in X, Y Z of UF beam 6 focal location.

OCT device 100 works on the principle of measuring differences in optical path length between its reference and sample arms. Therefore, passing the OCT through z-adjust 40 does not extend the z-range of OCT system 100 because the optical path length does not change as a function of movement of 42. OCT system 100 has an inherent z-range that is related to the detection scheme, and in the case of frequency domain detection it is specifically related to the spectrometer and the location of the reference arm 106. In the case of OCT system 100 used in FIG. 1, the z-range is approximately 1-2 mm in an aqueous environment. Extending this range to at least 4 mm involves the adjustment of the path length of the reference arm within OCT system 100. Passing the OCT beam 114 in the sample arm through the z-scan of z-adjust 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y Z should be conducted in order to match the OCT signal information to the UF focus location and also to the relate to absolute dimensional quantities.

Observation of an aim beam may also be used to assist the user to directing the UF laser focus. Additionally, an aim beam visible to the unaided eye in lieu of the infrared OCT and UF beams can be helpful with alignment provided the aim beam accurately represents the infrared beam parameters. An aim subsystem 200 is employed in the configuration shown in FIG. 1. The aim beam 202 is generated by a an aim beam light source 201, such as a helium-neon laser operating at a wavelength of 633 nm. Alternatively a laser diode in the 630-650 nm range could be used. The advantage of using the helium neon 633 nm beam is its long coherence length, which would enable the use of the aim path as a laser unequal path interferometer (LUPI) to measure the optical quality of the beam train, for example.

Once the aim beam light source generates aim beam 202, the aim beam 202 is collimated using lens 204. The size of the collimated beam is determined by the focal length of lens 204. The size of the aim beam 202 is dictated by the desired NA at the focus in the eye and the magnification of the beam train leading to the eye 68. Generally, aim beam 202 should have close to the same NA as UF beam 6 in the focal plane and therefore aim beam 202 is of similar diameter to the UF beam at the beamcombiner 34 location. Because the aim beam is meant to stand-in for the UF beam 6 during system alignment to the target tissue of the eye, much of the aim path mimics the UF path as described previously. The aim beam 202 proceeds through a half-wave plate 206 and linear polarizer 208. The polarization state of the aim beam 202 can be adjusted so that the desired amount of light passes through polarizer 208. Elements 206 & 208 therefore act as a variable attenuator for the aim beam 202. Additionally, the orientation of polarizer 208 determines the incident polarization state incident upon beamcombiners 126 and 34, thereby fixing the polarization state and allowing for optimization of the beamcombiners' throughput. Of course, if a semiconductor laser is used as aim beam light source 200, the drive current can be varied to adjust the optical power.

The aim beam 202 proceeds through a shutter 210 and aperture 212. The system controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of polarizer 206.

The aim beam 202 next passes through a beam conditioning device 214. Beam parameters such as beam diameter, divergence, circularity, and astigmatism can be modified using one or more well known beaming conditioning optical elements. In the case of an aim beam 202 emerging from an optical fiber, the beam conditioning device 214 can simply include a beam expanding telescope with two optical elements 216 and 218 in order to achieve the intended beam size and collimation. The final factors used to determine the aim beam parameters such as degree of collimation are dictated by what is necessary to match the UF beam 6 and aim beam 202 at the location of the eye 68. Chromatic differences can be taken into account by appropriate adjustments of beam conditioning device 214. In addition, the optical system 214 is used to image aperture 212 to a desired location such as a conjugate location of aperture 14.

The aim beam 202 next reflects off of fold mirrors 222 & 220, which are preferably adjustable for alignment registration to UF beam 6 subsequent to beam combiner 34. The aim beam 202 is then incident upon beam combiner 126 where the aim beam 202 is combined with OCT beam 114. Beamcombiner 126 reflects the aim beam 202 and transmits the OCT beam 114, which allows for efficient operation of the beamcombining functions at both wavelength ranges. Alternatively, the transmit and reflect functions of beamcombiner 126 can be reversed and the configuration inverted. Subsequent to beamcombiner 126, aim beam 202 along with OCT beam 114 is combined with UF beam 6 by beamcombiner 34.

A device for imaging the target tissue on or within the eye 68 is shown schematically in FIG. 1 as imaging system 71. Imaging system includes a camera 74 and an illumination light source 86 for creating an image of the target tissue. The imaging system 71 gathers images which may be used by the system controller 300 for providing pattern centering about or within a predefined structure. The illumination light source 86 for the viewing is generally broadband and incoherent. For example, light source 86 can include multiple LEDs as shown. The wavelength of the viewing light source 86 is preferably in the range of 700 nm to 750 nm, but can be anything which is accommodated by the beamcombiner 56, which combines the viewing light with the beam path for UF beam 6 and aim beam 202 (beamcombiner 56 reflects the viewing wavelengths while transmitting the OCT and UF wavelengths). The beamcombiner 56 may partially transmit the aim wavelength so that the aim beam 202 can be visible to the viewing camera 74. Optional polarization element 84 in front of light source 86 can be a linear polarizer, a quarter wave plate, a half-wave plate or any combination, and is used to optimize signal. A false color image as generated by the near infrared wavelength is acceptable.

The illumination light from light source 86 is directed down towards the eye using the same objective lens 58 and contact lens 66 as the UF and aim beam 6, 202. The light reflected and scattered off of various structures in the eye 68 are collected by the same lenses 58 & 66 and directed back towards beamcombiner 56. There, the return light is directed back into the viewing path via beam combiner and mirror 82, and on to camera 74. Camera 74 can be, for example but not limited to, any silicon based detector array of the appropriately sized format. Video lens 76 forms an image onto the camera's detector array while optical elements 80 & 78 provide polarization control and wavelength filtering respectively. Aperture or iris 81 provides control of imaging NA and therefore depth of focus and depth of field. A small aperture provides the advantage of large depth of field which aids in the patient docking procedure. Alternatively, the illumination and camera paths can be switched. Furthermore, aim light source 200 can be made to emit in the infrared which would not directly visible, but could be captured and displayed using imaging system 71.

Coarse adjust registration is usually needed so that when the contact lens 66 comes into contact with the cornea, the targeted structures are in the capture range of the X, Y scan of the system. Therefore a docking procedure is preferred, which preferably takes in account patient motion as the system approaches the contact condition (i.e. contact between the patient's eye 68 and the contact lens 66. The viewing system 71 is configured so that the depth of focus is large enough such that the patient's eye 68 and other salient features may be seen before the contact lens 66 makes contact with eye 68.

Preferably, a motion control system 70 is integrated into the overall control system 2, and may move the patient, the system 2 or elements thereof, or both, to achieve accurate and reliable contact between contact lens 66 and eye 68. Furthermore, a vacuum suction subsystem and flange may be incorporated into system 2, and used to stabilize eye 68. The alignment of eye 68 to system 2 via contact lens 66 may be accomplished while monitoring the output of imaging system 71, and performed manually or automatically by analyzing the images produced by imaging system 71 electronically by means of control electronics 300 via IO 302. Force and/or pressure sensor feedback may also be used to discern contact, as well as to initiate the vacuum subsystem.

Figure 2:
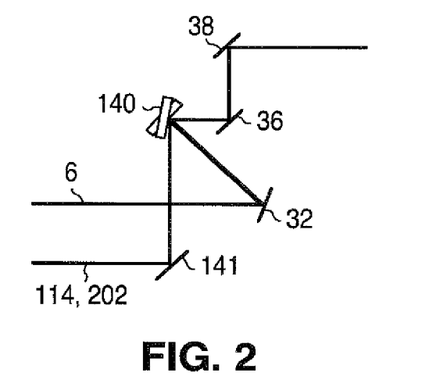
FIG. 2 is an optical diagram showing an alternative beam combining scheme.

An alternative beamcombining configuration is shown in the alternate embodiment of FIG. 2. For example, the passive beamcombiner 34 in FIG. 1 can be replaced with an active combiner 140 in FIG. 2. The active beamcombiner 34 can be a moving or dynamically controlled element such as a galvanometric scanning mirror, as shown. Active combiner 140 changes it angular orientation in order to direct either the UF beam 6 or the combined aim and OCT beams 202,114 towards the scanner 50 and eventually eye 68 one at a time. The advantage of the active combining technique is that it avoids the difficulty of combining beams with similar wavelength ranges or polarization states using a passive beam combiner. This ability is traded off against the ability to have simultaneous beams in time and potentially less accuracy and precision due to positional tolerances of active beam combiner 140.

Figure 3:
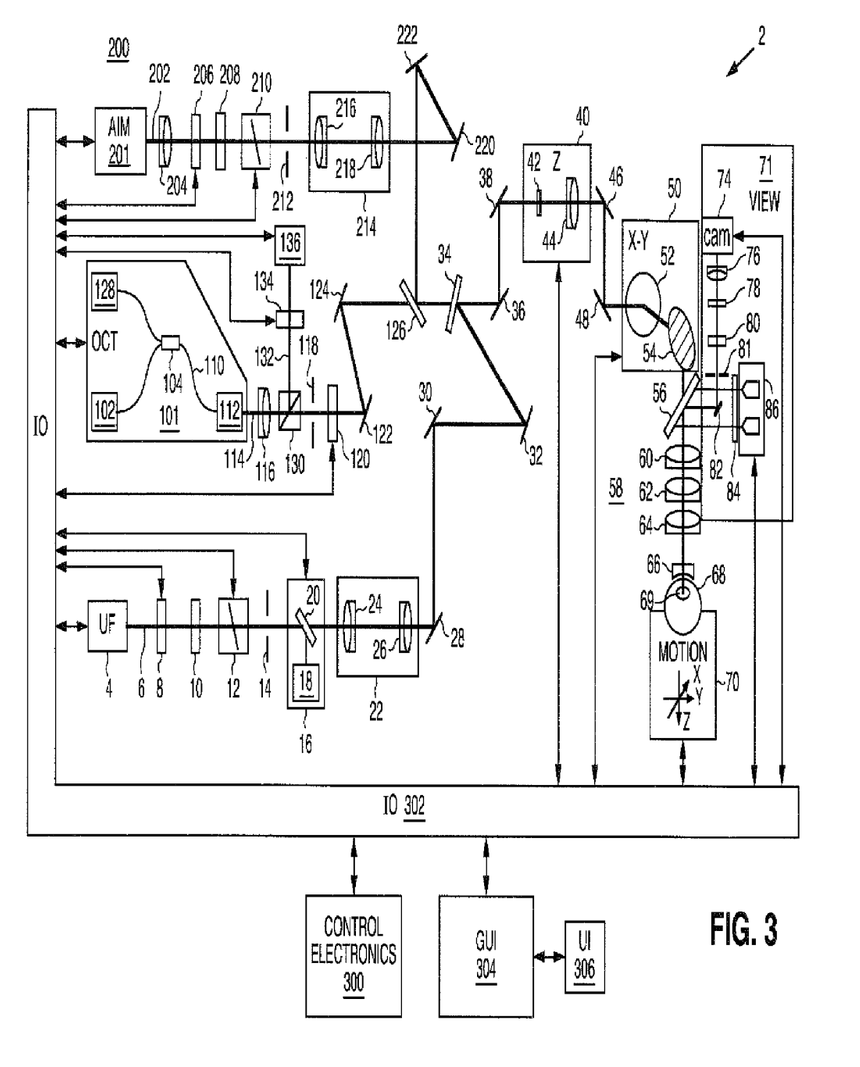
FIG. 3 is a schematic diagram of the optical beam scanning system with an alternative OCT configuration.

Another alternate embodiment is shown in FIG. 3 which is similar to that of FIG. 1 but utilizes an alternate approach to OCT 100. In FIG. 3, OCT 101 is the same as OCT 100 in FIG. 1, except that the reference arm 106 has been replaced by reference arm 132. This free-space OCT reference arm 132 is realized by including beamsplitter 130 after lens 116. The reference beam 132 then proceeds through polarization controlling element 134 and then onto the reference return module 136. The reference return module 136 contains the appropriate dispersion and path length adjusting and compensating elements and generates an appropriate reference signal for interference with the sample signal. The sample arm of OCT 101 now originates subsequent to beamsplitter 130. The potential advantages of this free space configuration include separate polarization control and maintenance of the reference and sample arms. The fiber based beam splitter 104 of OCT 101 can also be replaced by a fiber based circulator. Alternately, both OCT detector 128 and beamsplitter 130 might be moved together as opposed to reference arm 136.

Figure 4:
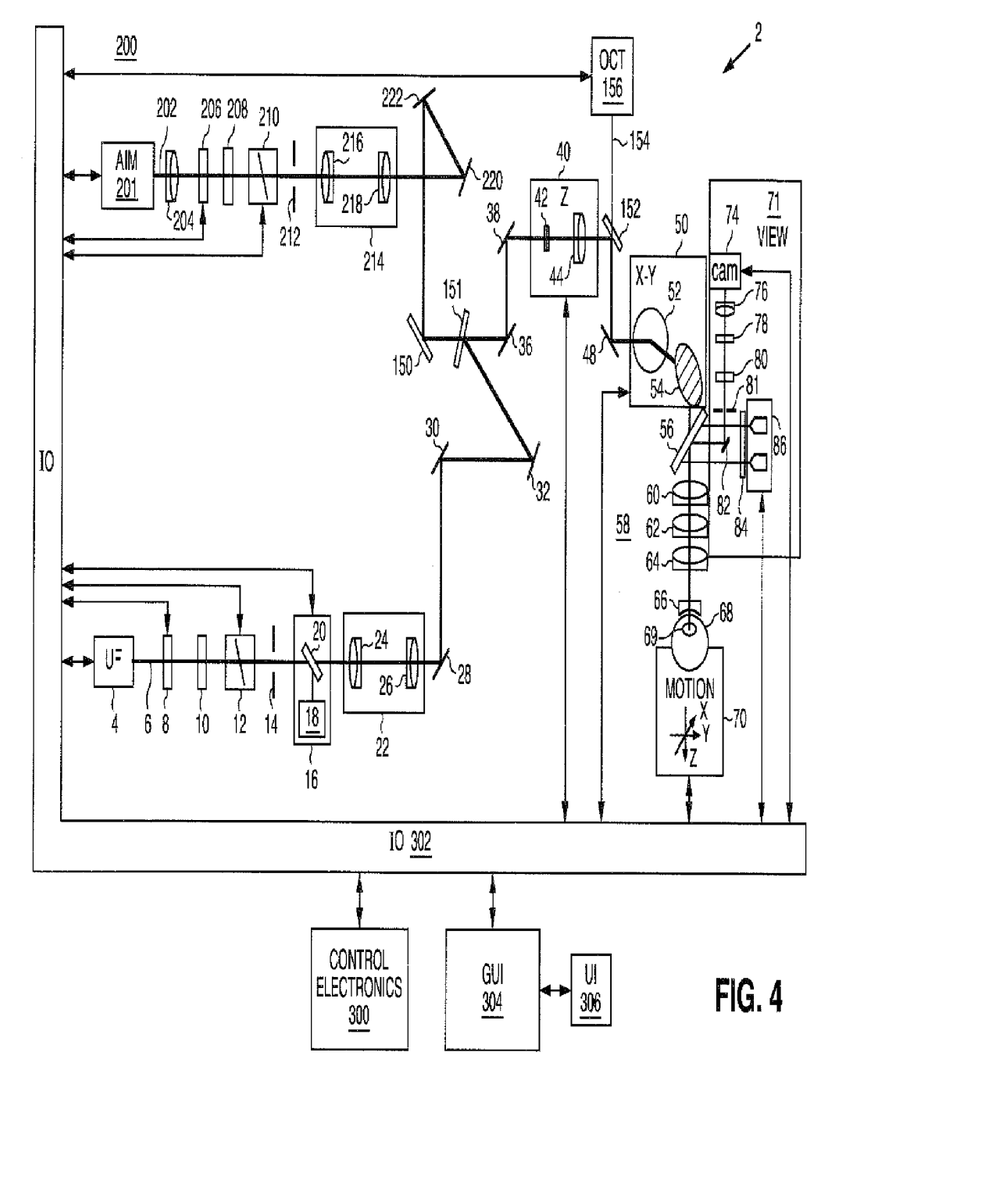
FIG. 4 is a schematic diagram of the optical beam scanning system with another alternative OCT combining scheme.

FIG. 4 shows another alternative embodiment for combining OCT beam 114 and UF beam 6. In FIG. 4, OCT 156 (which can include either of the configurations of OCT 100 or 101) is configured such that its OCT beam 154 is coupled to UF beam 6 after the z-scan 40 using beamcombiner 152. In this way, OCT beam 154 avoids using the z-adjust. This allows the OCT 156 to possibly be folded into the beam more easily and shortening the path length for more stable operation. This OCT configuration is at the expense of an optimized signal return strength as discussed with respect to FIG. 1. There are many possibilities for the configuration of the OCT interferometer, including time and frequency domain approaches, single and dual beam methods, swept source, etc, as described in U.S. Pat. Nos. 5,748,898; 5,748, 352; 5,459,570; 6,111,645; and 6,053,613 (which are incorporated herein by reference.)

Figure 5:
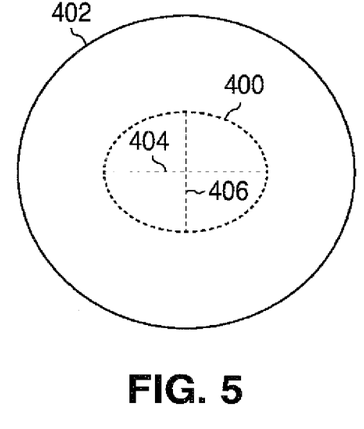
FIG. 5 is a top view diagram of a rotationally asymmetric capsulorhexis incision.

FIGS. 5 through 9 illustrate different aspects of an embodiment of the present invention, which can be implemented using the scanning system 2 described above. As shown in FIG. 5, a capsulorhexis incision 400 (which may be created using system 2) is tailored for astigmatism-correcting intraocular lenses (IOLs). Such astigmatism-correcting IOLs need to be placed not only at the correct location within the capsule 402 of the eye 68, but also oriented at the correct rotational/clocking angle. Thus, they have inherent rotational asymmetries, unlike spherical IOLs. The incision 400 shown in this example is elliptical, however, other shapes are also useful. Incision 400 may be made continuously, or piecewise to largely maintain the structural integrity of the lens-capsule apparatus of the patient's eye 68. Such incomplete incisions 400 may be thought of as perforated incisions, and may be made to be removed gently in order to minimize their potential to inadvertently extend the capsulorhexis. Either way, incision 400 is an enclosed incision, which for the purposes of this disclosure means that it starts and ends at the same location and encircles a certain amount of tissue therein. The simplest example of an enclosed incision is a circular incision, where a round piece of tissue is encircled by the incision. It follows therefore that an enclosed treatment pattern (i.e. generated by system 2 for forming an enclosed incision) is one that also starts and ends at the same location and defines a space encircled thereby.

One key feature of the enclosed incision 400 is that it includes a registration feature to orient the IOL that will be placed inside it. For the illustrated elliptical incision 400, it elliptical shape is it's registration feature, which allows for the accurate placement of an IOL by virtue of its inherent rotational asymmetry, unlike the desired circular outcome of a manual CCC. The elliptical major axis 404 and minor axis 406 of incision 400 are shown. Major axis 404 and minor axis 406 are not equal. Incision 400 may be made at any rotational angle relative to the eye 68 of a patient, although it is shown in this example to be in the plane of the iris with its major axis 404 lying along the horizontal. Incision 400 is intended to mate with one or more complementary registration features on an IOL. The ranging subsystem of system 2 (e.g. the OCT 100 subsystem) may be used to precisely define the surface of the capsule 402 to be incised. This may serve to isolate the laser pulses nominally to the vicinity of the targeted capsule 402 itself, thus minimizing the energy required and the treatment time and commensurately increasing patient safety and overall efficiency.

Figure 6:
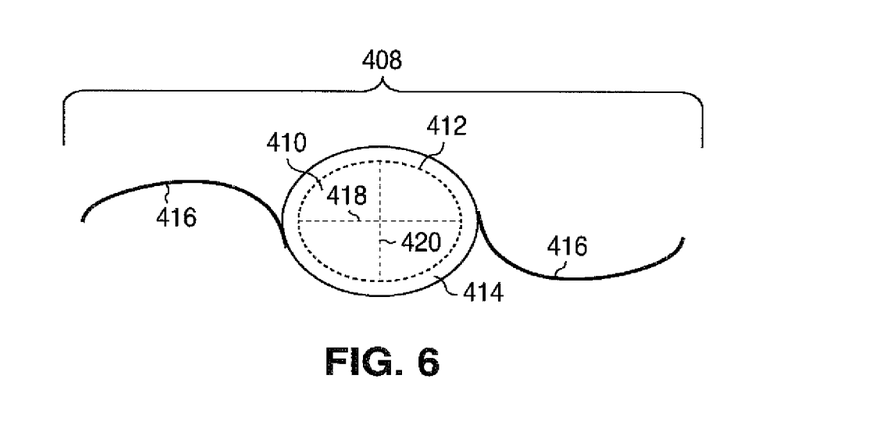
FIG. 6 is a top view diagram of a complementary rotationally asymmetric IOL.

As shown in FIG. 6, an IOL 408 includes an optic portion 410 used to focus light and a haptic 416 used to position the IOL 408. Optic 410 is a rotationally asymmetric lens (about its optical axis) that include an elliptically shaped peripheral sidewall or edge 412, the complementary registration feature that mates with elliptically shaped incision 400. In this example, the elliptically shaped edge 412 includes a major axis 418 and minor axis 420. Major axis 418 and minor axis 420 are not equal. Intraocular lens IOL 408 further contains surface 414 that serves to hold haptics element 416 and provide a resting place for capsule 402 to secure optic 410 of intraocular lens 408 in the proper orientation and position within the capsule 402 of a patient's eye 68. Surface 414 is shown as elliptical, but need not be. Haptics 416 provide stability and may serve to seat edge 412 of intraocular lens 408 in incision 400 by applying retaining force towards the anterior portion of capsule 402. Haptics 416 may be deployed in any orientation. The orientation of the cylindrical correction of optic 410 of intraocular lens 408 may be made to coincide with either its major axis 418 or its minor axis 420. In this way, intraocular lenses IOL 408 and optic 410 may be manufactured in a standardized manner and the rotational orientation of incision 400 and the spherical and cylindrical optical powers of optic 410 may be made to vary to suit the individual optical prescription of the eye 68 of a patient.

Figure 7:
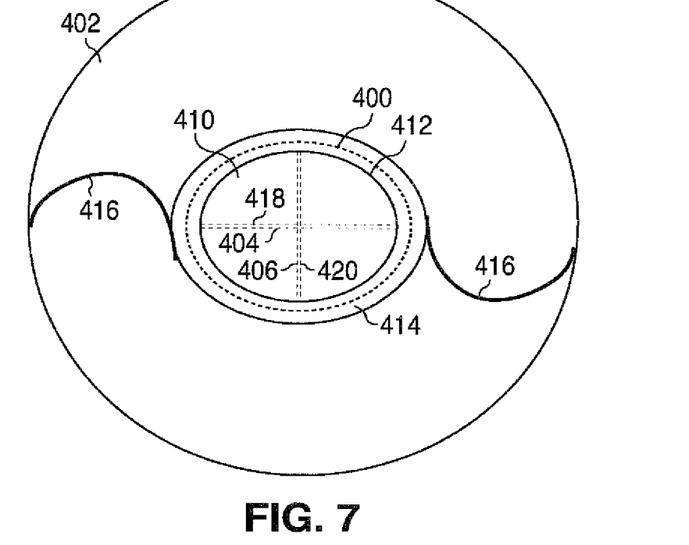
FIG. 7 is a top view the IOL of FIG. 6 positioned in the capsule of FIG. 5.

FIG. 7 shows the proper immediate disposition of intraocular lens 408 once installed into capsule 402 with mating registration features edge 412 and incision 400 engaged, and resting upon surface 414. Major axis 404 and major axis 418 are not of equal length. Minor axis 406 and minor axis 420 are not the same length, either. This is done to accommodate the fact the capsule 402 may contract somewhat subsequent to capsulorhexis incision. The difference between the lengths of these axes is intended to allow the capsule 402 to contract and still better seat intraocular lens 408 into capsule 402 via incision 400. These differences should be limited to allow for reasonable contraction, but not so much as to allow for significant rotation of intraocular lens 408. Typical values for these length differences may range from 100 µm to 500 µm, for example.

Figure 8:
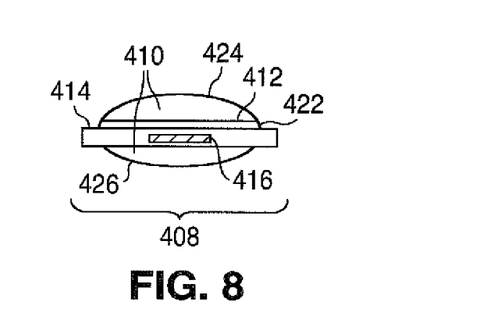
FIGS. 8 and 9 are side views of the rotationally asymmetric IOL of FIG. 6.

FIG. 8 shows a side view on the same intraocular lens 408 depicted in FIGS. 6 and 7. In this schematic representation, edge 412 is shown on the same side of optic 410 as surface 424 of intraocular lens 408. The surface 422 on intraocular lens 408 serves to maintain the integrity of fit between edge 412 and incision 400. Edge 412 is seen as the projection of surface 422 in the alternate view depicted in FIGS. 6 and 7. Optical axis 411 of optic 410 is shown. Haptics 416 lie along the line of sight in this view.

Figure 9:
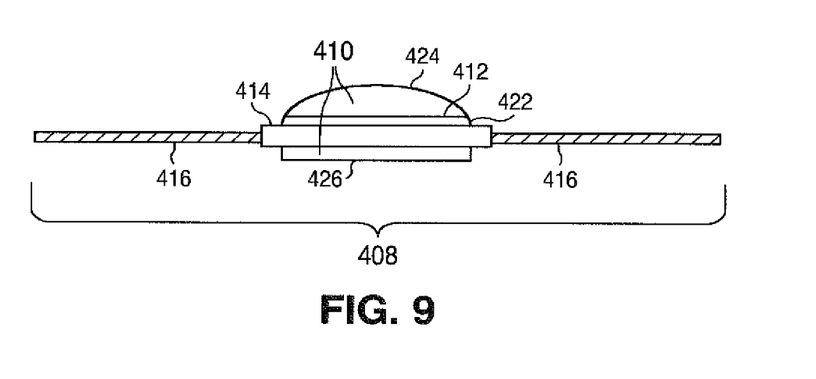

FIG. 9 is a side view of the lens configuration of FIG. 8, but rotated 90 degrees to show that displaying surface 426 is not curved in both directions (i.e. shaped as a cylindrical lens). This cylindrical or toric optical system of optic 410 provides cylindrical correction for the astigmatism of a patient. Haptics 416 lie perpendicular to the line of sight in this view.

Figure 10:
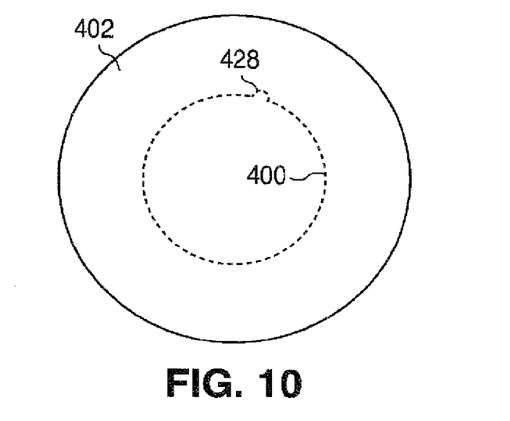
FIG. 10 is a top view diagram of a rotationally asymmetric capsulorhexis incision.
Figure 11:
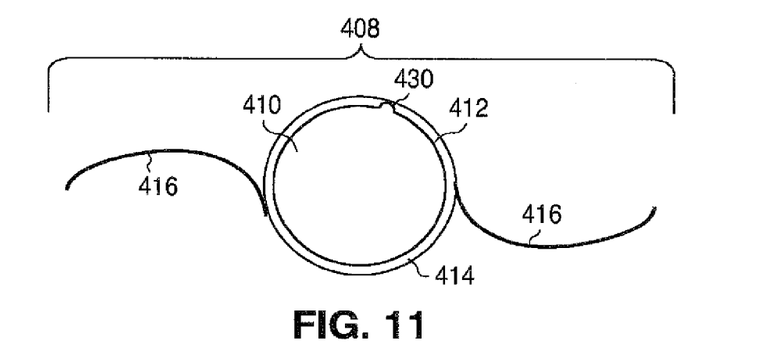
FIG. 11 is a top view diagram of a complementary rotationally asymmetric IOL.

FIG. 10 shows an alternate embodiment similar to the asymmetry of the example of FIG. 6, except that incision 400 includes a registration feature 428 formed as a notch extending from the otherwise round incision 400. Registration feature 428 serves to provide a means to locate a matching registration feature (i.e. a protrusion) on intraocular lens 410. The complementary registration feature 430 of IOL 408 including optic 410 is illustrated in FIG. 11. The shape of registration feature 428 is shown as half round for illustrative purposes only. Alternately, a teardrop shape, such as that shown in FIG. 15, for edge 412 and incision 400 is less likely to contain sharp edges and thus be less prone to inadvertent extension of the capsulorhexis. Many similar complementary shapes are possible and within the scope of the present invention. A benefit of the short pulse laser system described in FIG. 1 is that it may provide via a plasma-mediated ablation process smooth incisions 400 that are unlikely to extend.

In FIG. 11, registration feature 430 is intended to mate with registration feature 428 of incision 400. This serves to correctly locate optic 410 and maintain its rotational integrity. Here again edge 412 and surface 414 provide features to assure mechanical stability and proper orientation with respect to the capsule 402 of a patient's eye 68. Similar to the FIG. 6 description of the asymmetric major axes 404 & 418, registration feature 430 may be placed at an arbitrary rotational orientation to suit an individual prescription. Haptics 416 may be deployed in any orientation, as before.

Figure 12:
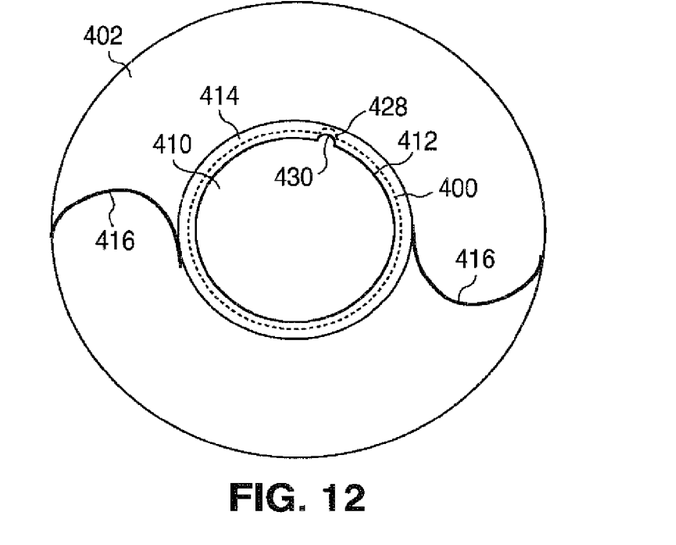
FIG. 12 is a top view of the IOL of FIG. 11 positioned in the capsule of FIG. 10.

FIG. 12 shows the proper immediate disposition of intraocular lens 408 once installed into capsule 402 via incision 400 with mating feature edge 412 engaged, similar to that shown in FIG. 7.

Figure 13:
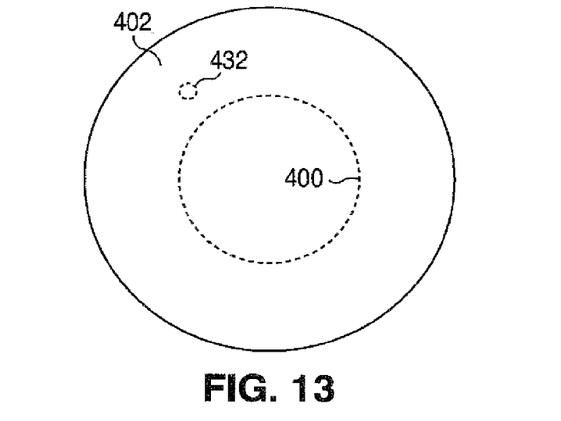
FIG. 13 is a top view diagram of a rotationally asymmetric capsulorhexis incision.

FIG. 13 shows an alternate embodiment similar to that of FIGS. 6 & 10 with the addition of a registration incision 432 (formed by a registration pattern of treatment light generated by system 2) that is separate and distinct from capsulorhexis incision 400. As before, registration incision 432 serves to provide a means to locate a matching registration feature on intraocular lens 408.

Figure 14:
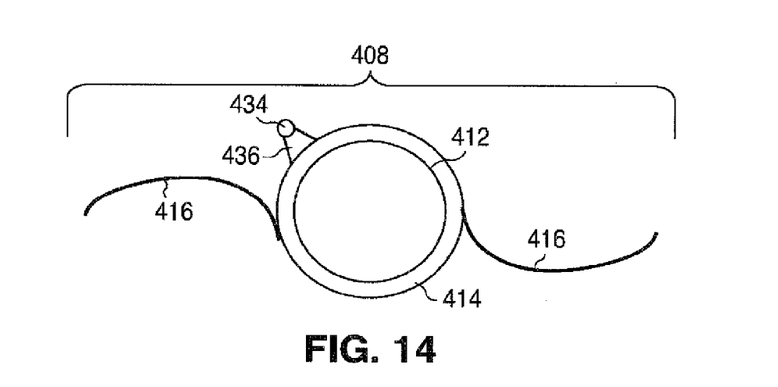
FIG. 14 is a top view shows a diagram of a complementary rotationally asymmetric IOL.

FIG. 14 shows an alternate embodiment similar to that of FIG. 11, with post 434 that sits in the registration incision 432 and atop strut 436 away from optic 410 on intraocular lens 408. Post 434 and strut 436 are shown as being tilted away from the normal between haptics 416, but need not be. Many such similar complementary configurations are possible and within the scope of the present invention.

Figure 15:
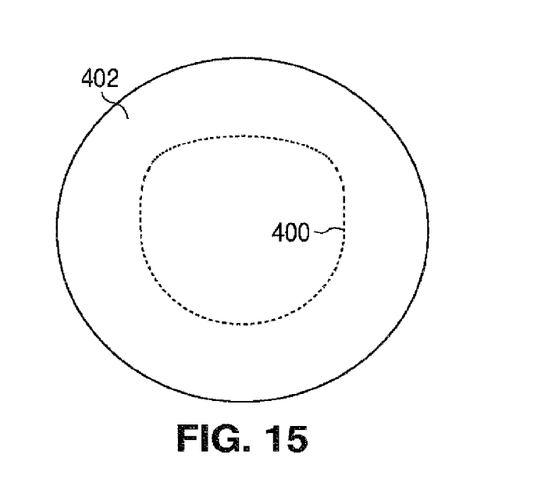
FIG. 15 is a top view diagram of a rotationally asymmetric capsulorhexis incision.

IOL 408 can also mate with the capsulorhexis incision by way of a circumferential flange. The shape of the capsulorhexis incision 400 may be made to orient the IOL 408 to achieve cylindrical corrections, as shown schematically in FIG. 15. The asymmetric incision 400 of FIG. 15 is similar to that of FIGS. 5, 10 and 13 with the addition that it is intended to mate with a flange on intraocular lens 408 rather than an edge 412 and a surface 414.

Figure 16:
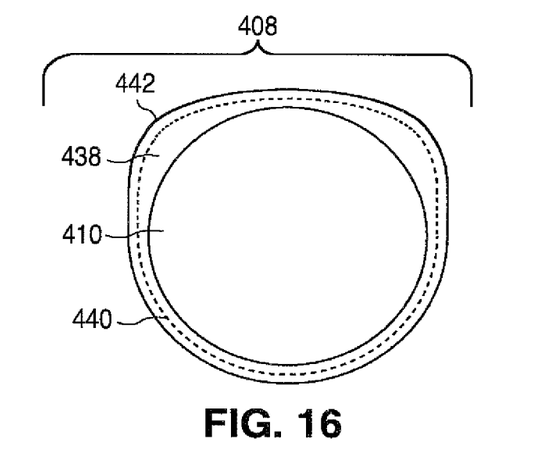
FIG. 16 is a top view diagram of a complementary rotationally asymmetric IOL.

FIG. 16 shows intraocular lens 408 utilizing a flange 438 to mate with incision 400. As shown, intraocular lens 408 is comprised of optic 410 and flange 438. This flange 438 may be circumferential, as shown, but need not be. It may simply lie atop optic 410 and serve the same purpose of mating and retaining intraocular lens 408 within capsule 402. Flange 438 contains groove 440 to seat the capsule 402 in incision 400. Rotationally asymmetric groove 440 serves to accurately position and retain intraocular lens 408 within incision 400 at the correct rotational orientation for the individual astigmatic prescription. This optical correction is achieved using optic 410. Alternately, groove 440 may be a created between flange 438 and optic 410 (rather than within flange 438, as shown) when flange 438 lies atop intraocular lens 408. Such an intraocular lens 408 may be used in "bag-in-the-lens" surgeries.

Figure 17:
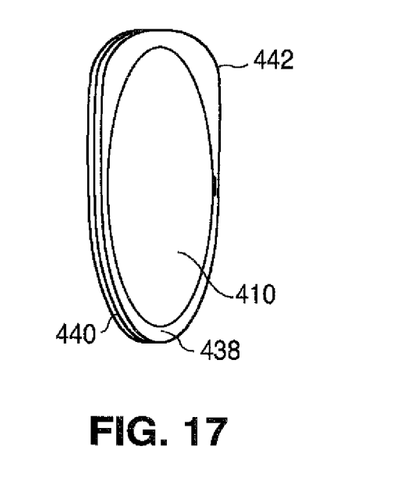
FIG. 17 is a perspective view of the rotationally asymmetric IOL of FIG. 16.
Figure 18:
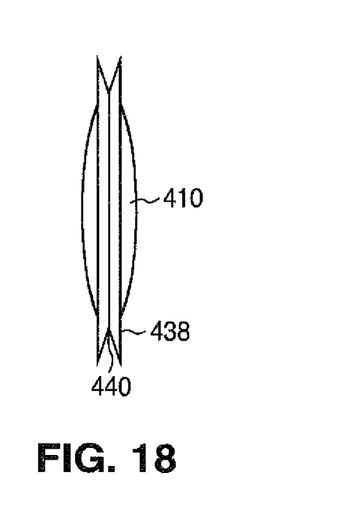
FIG. 18 is a side view of the rotationally asymmetric IOL of FIG. 16.

FIGS. 17 and 18 show the same configuration as that of FIG. 16, but from different viewing perspectives to better illustrate groove 440. Groove 440 may be made to engage incision 400 continuously, as shown, or discontinuously by providing notches cut into flange 438. Such notches may serve to more easily initiate the engagement of flange 438 with capsule 402 via incision 400. Alternately, flange 438 could be made such that the depth between its edge and groove 440 varies along its circumference. This way, a region of shallow depth could be used as a starting point for more easily engaging intraocular lens 408 with capsule 402 via incision 400.

Figure 19:
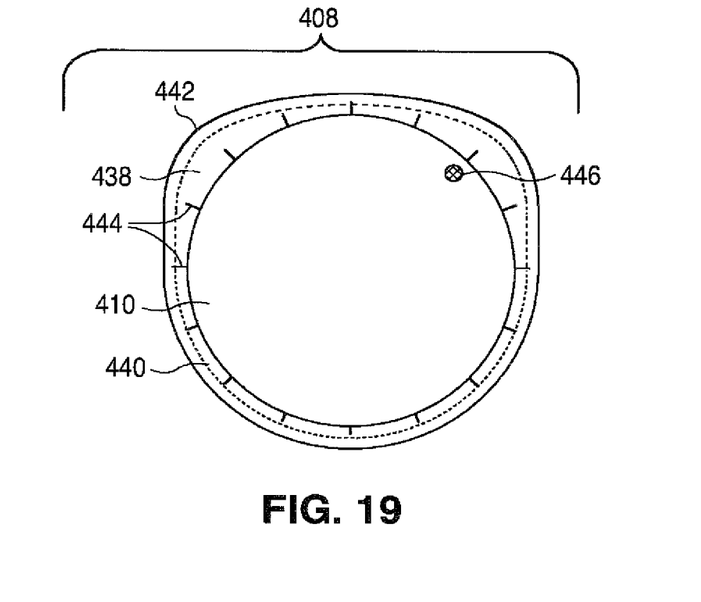
FIG. 19 is a top view diagram of a rotationally asymmetric IOL.

FIG. 19 shows an alternate embodiment that is similar to that of FIG. 16, but where optic 410 may be made to rotate within flange 438. To align the rotation of optic 410, angular alignment marks 444 are displayed on flange 438 and a complementary alignment mark 446 is displayed on optic 410. In this manner, intraocular lens 408 and optic 410 may be manufactured in a standardized manner and one may rotate optic 410 relative to its surrounding flange 438 to provide astigmatic correction to suit the individual prescription. Alignment marks 444 are shown at 22.5° intervals, but may be otherwise. Alignment marks 444 and 446 may be etched into the materials of their host elements, or alternately imprinted upon them.

Figure 20:
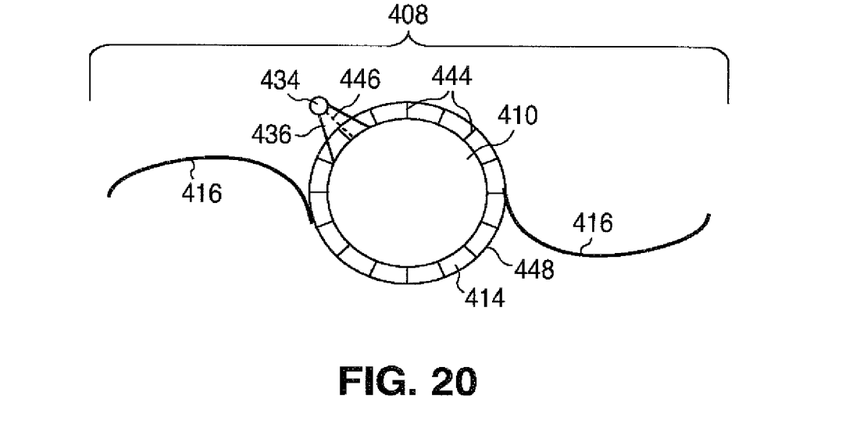
FIG. 20 is a top view diagram of a rotationally asymmetric IOL.

FIG. 20 shows one further alternate embodiment that is similar to that of FIGS. 14 and 19, where optic 410 may be made to rotate within ring 448. In this illustrative example, post 434 and strut 436 are integral to optic 410, and contain alignment mark 446. Ring 448 contains haptics 416 and surface 414 as before but now also alignment marks 444. Alignment mark 446 on strut 436 of optic 410 facilitates the rotational orientation of astigmatic correcting optic 410. In this manner, the ultimate orientation of intraocular lens 408 within capsule 402 of the eye of a patient via incision 400 that may be made in any orientation. Many such similar complementary configurations are possible and within the scope of the present invention.

It is to be understood that the present invention is not limited to the embodiment(s) described above and illustrated herein, but encompasses any and all variations falling within the scope of the appended claims. For example, references to the present invention herein are not intended to limit the scope of any claim or claim term, but instead merely make reference to one or more features that may be covered by one or more of the claims. All the optical elements downstream of scanner 50 shown in FIGS. 1, 3 and 4 form a delivery system of optical elements for delivering the beam 6, 114 and 202 to the target tissue. Conceivably, depending on the desired features of the system, some or even most of the depicted optical elements could be omitted in a delivery system that still reliably delivers the scanned beams to the target tissue. Protrusion registrations features could be replaced with indentations (i.e. notches), and vice versa.

What is claimed is:

1. A system for treating a lesion on target eye tissue, comprising:
   a. a light source for producing a laser beam;
   b. one or more scanning elements configured to direct a focal point of a laser beam produced by the light source to various portions of a lens capsule of an eye of a patient; and
   c. a controller operatively coupled to the light source and to the one or more scanning elements, wherein the controller is programmed to operate the one or more scanning elements to cause a laser beam produced by the light source to create a capsulotomy and at least one intraocular lens registration feature within a lens capsule of a patient's eye,
   wherein, taken together, the capsulotomy and the at least one registration feature has rotational asymmetry.

2. The system of claim 1, wherein the at least one registration feature is capable of mating with a complimentary feature of an intraocular lens to orient the intraocular lens.

3. The system of claim 1, wherein the capsulotomy comprises the at least one lens registration feature.

4. The system of claim 3, wherein the at least one lens registration feature comprises an asymmetric shape of the capsular incision.

5. The system of claim 1, wherein the at least one registration feature comprises a feature that is continguous with at least a portion of the capsulotomy.

6. The system of claim 5, wherein the feature comprises a notch or protrusion adjacent a portion of the capsulotomy.

7. The system of claim 1, wherein the light source is a pulsed laser.

8. The system of claim 1, wherein the laser beam has a pulse width of between about 100 femtoseconds and about 10,000 femtoseconds.

9. The system of claim 1, wherein the light source produces a laser beam having a wavelength between about 1,010 nanometers and about 1,100 nanometers.

10. The system of claim 1, wherein the various portions of the lens capsule of the patient's eye are selected from the group consisting of an anterior capsular portion and a posterior capsular portion.

11. The system of claim 1, further comprising an optical system configured to acquire image information regarding one or more structures of the eye.

12. The system of claim 11, wherein the one or more structures of the eye are selected from the group consisting of: a cornea, an iris, a lens capsule, and a crystalline lens.

13. The system of claim 11, wherein the image information is selected from the group consisting of: position information, shape information, and size information of the one or more structures of the eye.

14. The system of claim 11, wherein the optical system comprises a component selected from the group consisting of: an optical coherence tomography system, a Purkinje imaging system, a Scheimpflug imaging system, and a camera.

15. The system of claim 1, wherein the controller is programmed to create the capsulotomy to have a shape selected from the group consisting of: a substantially circular shape, a substantially elliptical shape, and a partially circular shape having a noncircular portion.

16. The system of claim 1, wherein the controller is programmed to create the respective capsulotomy and intraocular lens registration feature by creating one or more incisions with the laser beam.

17. The system of claim 10, wherein the controller is programmed to create at least a portion of the one or more incisions using a continuous pattern.

18. The system of claim 10, wherein the controller is programmed to create at least a portion of the one or more incisions using a discontinuous pattern.

19. The system of claim 10, wherein the controller is programmed to receive user input data and to thereafter automatically operate the one or more scanning elements based at least in part on the received user input data.

20. A system for surgery on a tissue of a patient's eye, comprising:

a. an imaging system for generating image data of a patient's lens;
b. a light source for producing a laser beam;
c. one or more scanning elements for directing a focal point of a laser beam produced by the light source to various portions of a lens capsule of an eye of a patient; and
d. a controller operatively coupled to the imaging assembly, the light source and the one or more scanning elements, wherein the controller is programmed to operate the imaging system so as to acquire image data of the patient's lens; and operate the one or more scanning elements to guide a laser beam produced by the light source based at least in part on the image data so as to create within an anterior lens capsule of a patient's eye (1) a capsulotomy and (2) an intraocular lens registration feature, wherein, taken together, the capsulotomy and the at least one registration feature has rotational asymmetry.

21. The system of claim 20, wherein the at least one registration feature is capable of mating with a complimentary feature of an intraocular lens to orient the intraocular lens.

* * * * *